United States Patent [19]

Nienburg et al.

[11] 3,933,920

[45] Jan. 20, 1976

[54] PRODUCTION OF α, ω-DIALDEHYDES

[75] Inventors: Hans Juergen Nienburg, Heidelberg; Rudolf Kummer, Frankenthal, both of Germany

[73] Assignee: BASF Aktiengesellschaft, Ludwigshafen (Rhine), Germany

[22] Filed: Mar. 12, 1974

[21] Appl. No.: 450,284

[30] Foreign Application Priority Data

Mar. 24, 1973 Germany............................ 2314694

[52] U.S. Cl... 260/604 HF; 260/78.4 R; 260/530 R; 260/585 C; 260/635 A; 260/637 R; 423/417
[51] Int. Cl.² .......................................... C07C 47/12
[58] Field of Search ............................... 260/604 HF

[56] References Cited
UNITED STATES PATENTS

| | | |
|---|---|---|
| 2,738,370 | 3/1956 | Staib et al..................... 260/604 HF |
| 2,748,167 | 5/1956 | Hagemeyer et al............ 260/604 HF |
| 2,985,504 | 5/1961 | Orchin.......................... 260/604 HF |

Primary Examiner—Joseph E. Evans
Attorney, Agent, or Firm—Johnston, Keil, Thompson & Shurtleff

[57] ABSTRACT

An improved process for the production of α,ω-dialdehydes by reaction of linear α,ω-diolefins having isolated double bonds with carbon monoxide and hydrogen at elevated temperature and at superatmospheric pressure in the presence of a cobalt carbonyl complex in which the improvement consists in supplying the cobalt to the reaction as cobalt carbonyl hydride dissolved in the α,ω-diolefin to be used or in an inert organic solvent and carrying out the reaction at a temperature of from 70° to 130°C.

7 Claims, No Drawings

PRODUCTION OF α, ω-DIALDEHYDES

This application discloses and claims subject matter described in German patent application No. P 23 14 694.3, filed March 24, 1973, which is incorporated herein by reference.

The invention relates to an improved process for the production of an α,ω-dialdehyde by reaction of a linear α,ω-diolefin having isolated double bonds with carbon monoxide and hydrogen at elevated temperature and superatmospheric pressure in the presence of a cobalt carbonyl complex.

The double hydroformylation of diolefins has been investigated in a number of instances but hitherto has not led to unambiguous results. Thus it is known from the dissertation "Hydroformylierung mehrfach ungesättigter Kohlenwasserstoffe mit isolierten Doppelbindungen" ("Hydroformylation of plurally unsaturated hydrocarbons having isolated double bonds") by A. Lamping, Aachen, 1971, page 69, that experiments for plural hydroformylation of olefins having isolated double bonds with cobalt carbonyl and tertiary phosphines as catalyst have been abortive. Only monohydroformylation products could be isolated. Moreover in Chemie-Ingenieur-Technik, volume 44, 1972, pages 711 and 712 it is stated that dienes having isolated double bonds can only be hydroformylated into the corresponding diols in good yields by using rhodium-carbonyl complexes which have been modified with tertiary amines. The use of complicated rhodium catalysts which moreover are very expensive is avoided as far as possible in industry. In "Chemie und Technologie der Monoolefine" "Chemistry and Technology of the Monoolefins" by A. Singer, 1957, page 655, reference is made to the fact that branched diolefins having isolated double bonds can be hydroformylated twice, but yields of only 35% of bishydroformylated products are obtained. Adoption of this procedure for α,ω-diolefins, which are easily isomerizable, does not appear to be indicated because isomerization readily takes place under the influence of cobalt catalysts.

The object of the invention is to provide a process in which inexpensive cobalt catalysts are used for the hydroformylation of α,ω-diolefins and in which nonetheless isomerization occurs only to a negligible extent. Another object of the invention is to provide a process in which α,ω-bishydroformylation products are obtained in high yields.

In accordance with this invention these and other objects and advantages are achieved in an improved process for the production of α,ω-dialdehydes by reaction of a linear α,ω-diolefin having isolated double bonds with carbon monoxide and hydrogen at elevated temperature and at superatmospheric pressure in the presence of a cobalt carbonyl complex wherein the improvement comprises supplying the cobalt to the reaction as cobalt carbonyl hydride dissolved in the α,ω-diolefin to be used or in an inert organic solvent and carrying out the reaction at a temperature of from 70° to 130°C.

It is preferred to use as the starting material a linear α,ω-diolefin of 5 to 20 and particularly from 5 to 12 carbon atoms. Examples of suitable diolefins are hexadiene-1,5, octadiene-1,7, decadiene-1,9 and hexadecadiene-1,15.

Carbon monoxide and hydrogen are used as a rule in the stoichiometric ratio with respect to the diolefin. It is advantageous however to use the gas mixture in excess, for example of up to 100 mole%. The ratio of carbon monoxide to hydrogen in the gas mixture used is generally from 4:1 to 1:4 and preferably from 2:1 to 1:2.

The reaction is carried out at a temperature of from 70° to 130°C. Particularly good results are obtained by maintaining a temperature of from 100° to 120°C. It is advantageous to maintain a pressure of from 100 to 400 atmospheres during the reaction. Pressures of from 200 to 300 atmospheres have proved to be particularly suitable.

Cobalt is supplied to the reaction in the form of cobalt carbonyl hydride dissolved in the α,ω-diolefin to be used or in an inert solvent. The cobalt is advantageously used in an amount of from 0.1 to 1% by weight, calculated as cobalt and based on the reaction mixture, as cobalt carbonyl hydride.

In addition to the α,ω-diolefin used as the starting material, hydrocarbons, alkanols, alkanals, esters or ethers are preferably used as inert solvents.

Suitable hydrocarbons include saturated paraffin hydrocarbons, for example paraffins of 3 to 20 carbon atoms such as propane, butanes or $C_8$ to $C_{10}$, $C_{10}$ to $C_{12}$ or $C_{16}$ to $C_{18}$ distillation cuts, and also cycloalkanes of 6 to 12 carbon atoms, particularly cyclohexane and aromatic hydrocarbons of 6 to 8 carbon atoms such as benzene, toluene, xylenes or ethylbenzene.

Alkanols and alkanals of 4 to 20 carbon atoms are preferred. Acetals of the said alkanals are also suitable.

Further suitable solvents are fatty acid esters of alkanols provided they are liquid under the reaction conditions, and also dialkyl ethers such as dibutyl ether.

It is preferred to use aliphatic and aromatic hydrocarbons as solvents.

It has proved to be particularly suitable to use solutions of cobalt carbonyl hydride which have been prepared by treating, in a first stage, an aqueous cobalt salt solution with carbon monoxide and hydrogen at a temperature of from 80° to 160°C and at a pressure of from 200 to 400 atmospheres in the presence of activated carbon, a zeolite or a basic ion exchanger which has been loaded with cobalt carbonyl, extracting the resulting solution of cobalt carbonyl hydride either together with the gas mixture or after separating the gas mixture in a second stage at a temperature of from 20° to 100°C and at a pressure of from 1 to 400 atmospheres with the above solvents provided they are insoluble in water or are only partly miscible with water, and separating the aqueous phase. The solution of cobalt carbonyl hydride in an organic solvent thus obtained is outstandingly suitable for hydroformylation.

Examples of suitable types of activated carbon are peat charcoal, animal charcoal or sugar charcoal. Peat carbon has proved to be particularly suitable. Preferred basic ion exchanges are those which contain primary, secondary or tertiary amino groups. Basic ion exchangers based on polystyrene and which contain tertiary amino groups or quaternary amino groups are of particular significance. Weakly to strongly basic ion exchangers, for example those known under registered Trade Marks AMBERLIT IR 45 or DOWEX 4 are particularly suitable. Macroreticular types such as those known under registered Trade Marks AMBERLYST A 21, LEWATIT MP 62, LEWATIT MP 64, IMAC A 20, CEROLIT G, AMBERLIT IRA 93 and AMBERLYST A 26 are of special industrial importance. The activated carbon, zeolites or basic ion exchangers are conveniently loaded with cobalt carbonyl to the point of saturation. This is generally achieved by passing the aqueous solution of the cobalt salt together with the said gas mixture of carbon monoxide and hydrogen under the said reaction conditions over the active carbon, zeolite or basic ion exchanger until it is saturated, i.e. until cobalt carbonyl and cobalt carbonyl hydride are detected analytically in the discharge.

When an active carbon or zeolite is used temperatures of from 100° to 160°C have proved to be particularly favorable. On the other hand it is advisable to maintain temperatures of from 100° to 120°C when using basic ion exchangers. Pressures of from 2 to 300 atmospheres have proved to be particularly advantageous.

The treatment is generally carried out in a treatment zone which conveniently has a ratio of length to diameter of from 5:1 to 50:1. It is advantageously effected at a rate of from 1.5 to 50 g of cobalt in the form of the salt used per hour per kilogram of activated carbon, zeolite or basic ion exchanger.

The aqueous cobalt salt solution is one of a fatty acid salt which is soluble in water and particularly of a formate, acetate, propionate or butyrate. Cobalt acetate and formate have proved to be particularly suitable. It is convenient to start from solutions which contain from 0.5 to 3% by weight of cobalt calculated as metal.

The aqueous solution containing cobalt salt and cobalt carbonyl hydride obtained in the first stage is extracted together with the gas mixture or after the separation of the same with one of the above solvents which is insoluble in water or only slightly miscible with water in a second stage at a temperature of from 20° to 100°C. Extraction may be carried out cocurrently or countercurrently. Cocurrent extraction has proved to be particularly suitable, a turbulent flow being maintained in the extraction zone, for example by Raschig rings or similar tower packing.

The extraction may be carried out without separation of the mixture of carbon monoxide and hydrogen at the same temperature as in the first stage. When the mixture of carbon monoxide and hydrogen is separated the extraction may be carried out at atmospheric pressure or slightly superatmospheric pressure, for example up to 10 atmospheres, with the use of a gas rich in carbon monoxide.

After the extraction the organic phase is separated from the aqueous phase by conventional methods. The organic phase generally contains from 0.05 to 2% by weight of cobalt, mainly in the form of cobalt carbonyl hydride.

From the $\alpha,\omega$-dialdehydes prepared according to the process of the invention it is possible to obtain, by reaction with ammonia in the presence of a hydrogenation catalyst and hydrogen, $\alpha,\omega$-diamines which are known as starting materials for highly polymerized polyamides. The $\alpha,\omega$-dialdehydes obtained may also be readily hydrogenated to the corresponding $\alpha,\omega$-diols or oxidized to dicarboxylic acids which are also starting materials for polymers.

The process according to the invention is illustrated by the following Examples.

EXAMPLE 1

100 ml of a precarbonylated cobalt formate solution (which contains 0.75 g of cobalt as cobalt carbonyl hydride) is passed per hour into a flask (capacity 400 ml) which is flushed with carbon monoxide. The flask is also charged hourly with a mixture of 98 g of octadiene-1,7 and 350 g of benzene. The mixture leaving the flask separates into two phases in a dwell tank. The organic phase is separated and contains 0.15% by weight of cobalt as a cobalt carbonyl complex.

450 g of the organic phase is hydroformylated with an equimolar mixture of carbon monoxide and hydrogen at a temperature of 120°C and a total pressure of 280 bar in an autoclave provided with a stirrer. It is 3 hours before all the gas has been absorbed.

The hydroformylation discharge has 5 ml of phosphoric acid added to it and is then freed from cobalt with steam. Since the aldehydes obtained are fairly unstable they are converted for easier identification into the corresponding diols by adding 1 liter of ethanol and hydrogenating with hydrogen at 150°C and a total pressure of 280 bar with 50 g of Raney nickel. The crude alcohol mixture is fractionally distilled after separation of the hydrogenation catalyst and the diluent. A first runnings passing over at up to 144°C at 3 mm Hg and consisting of hydrocarbon and nonanol (22 g), a decanediol fraction (110 g) which passes over at from 144° to 145°C at 3 mm Hg and 5 g of residue are obtained. The decanediol fraction consists, according to gas chromatographic analysis, of 70% of decanediol-1,10 and 30% of other isomers and particularly of 2-methylnonanediol-1,9.

70 g of decanediol-1,10 of a purity of 98% is recovered from the diol mixture by fractional crystallization from ether.

EXAMPLE 2

The procedure of Example 1 is followed but the reaction mixture obtained after removal of cobalt is investigated without having been hydrogenated. The following composition is established by gas chromatography:

hydrocarbon ($C_8$) less than 1%;
mixture of isononanol and an unknown compound (probably a cycloketone) 7.8%;
n-nonanol 8.2%;
branched decanedials 23.8%;
decanedial-1,10 56.8%;
mixed decanolals and formates of the same 2.5%.

Fractional distillation after removal of the solvent gives a first runnings (26 g) passing over at 100°C at 0.5 mm Hg, a dialdehyde main runnings (86 g) passing over at from 100° to 130°C at 0.5 mm Hg and 21 g of substances of higher boiling point and residue. The residue has for the most part been formed by decomposition of the very sensitive dialdehyde during the distillation as comparison with Example 1 shows.

We claim:

1. An improved process for the production of an $\alpha,\omega$-dialdehyde by reaction of a linear $\alpha,\omega$-diolefin having isolated double bonds with carbon monoxide and hydrogen at elevated temperature and at superatmospheric pressure in the presence of a cobalt carbonyl complex, wherein the improvement comprises supplying the cobalt to the reaction in the form of cobalt carbonyl hydride which is dissolved in the $\alpha,\omega$-diolefin to be used or in an inert organic solvent and carrying out the reaction at a temperature of from 70° to 130°C.

2. A process as claimed in claim 1 wherein a temperature of from 100° to 120°C is maintained.

3. A process as claimed in claim 1 wherein a pressure of from 100 to 400 atmospheres is maintained.

4. A process as claimed in claim 1 wherein the $\alpha,\omega$-diolefin used has five to twenty carbon atoms.

5. A process as claimed in claim 1 wherein the amount of cobalt used is from 0.1 to 1% by weight of cobalt, calculated as metal and based on the reaction mixture, the cobalt being used in the form of cobalt carbonyl hydride.

6. A process as claimed in claim 1 wherein said diolefin is a linear α,ω-diolefin hydrocarbon having 5 to 20 carbon atoms.

7. A process as claimed in claim 1 wherein said diolefin is a linear α,ω-diolefin hydrocarbon having 5 to 20 carbon atoms and the pressure is 100 to 400 atmospheres.

* * * * *